(12) United States Patent
Schiller et al.

(10) Patent No.: US 12,649,023 B2
(45) Date of Patent: Jun. 9, 2026

(54) AUTOMATIC EMPTYING OF A DIALYZER FOLLOWING A BLOOD TREATMENT THERAPY

(71) Applicant: B. Braun Avitum AG, Melsungen (DE)

(72) Inventors: Joana Sophie Schiller, Rheine (DE); Tobias Wuerschmidt, Hann. Muenden (DE)

(73) Assignee: B. Braun Avitum AG, Melsungen (DE)

( * ) Notice: Subject to any disclaimer, the term of this patent is extended or adjusted under 35 U.S.C. 154(b) by 572 days.

(21) Appl. No.: 18/030,303

(22) PCT Filed: Oct. 1, 2021

(86) PCT No.: PCT/EP2021/077052
§ 371 (c)(1),
(2) Date: Apr. 5, 2023

(87) PCT Pub. No.: WO2022/073857
PCT Pub. Date: Apr. 14, 2022

(65) Prior Publication Data
US 2023/0372595 A1 Nov. 23, 2023

(30) Foreign Application Priority Data
Oct. 7, 2020 (DE) ..................... 10 2020 126 303.1

(51) Int. Cl.
*A61M 1/36* (2006.01)
(52) U.S. Cl.
CPC .................................. *A61M 1/365* (2014.02)
(58) Field of Classification Search
CPC .. A61M 1/365; A61M 1/3649; A61M 1/3652; A61M 1/3644; A61M 1/3643;
(Continued)

(56) References Cited

U.S. PATENT DOCUMENTS 4,267,040 A * 5/1981 Schal .................. A61M 1/1639
210/257.2
7,985,196 B2 * 7/2011 Kopperschmidt .. A61M 1/3644
210/645
(Continued)

FOREIGN PATENT DOCUMENTS

CN 103517724 A 1/2014
CN 107296989 A 10/2017
(Continued)

OTHER PUBLICATIONS

Office Action received in Chinese Application No. 202180068955.9 dated Jul. 19, 2025, with translation, 17 pages.
(Continued)

*Primary Examiner* — Jessica Arble
*Assistant Examiner* — Seth Han
(74) *Attorney, Agent, or Firm* — Christopher A. Rothe; CM Law

(57) ABSTRACT

An extracorporeal blood treatment apparatus includes an extracorporeal circuit, a dialysis fluid circuit, and a dialyzer. A blood side and a dialysis fluid side of the dialyzer are separated by a membrane. A control unit automatically empties the dialyzer by setting a reduced pressure or negative pressure in the dialysis fluid circuit and by a passage of fluid from the blood side to the dialysis fluid side via the membrane. Once fluid has passed from the blood side to the dialysis fluid side and the blood side has been emptied, the control unit brings about a passage of air from the blood side to the dialysis fluid side via the membrane, and a displacement of the fluid out of the dialysis fluid side toward a dialysis fluid outflow by continued setting of the reduced pressure or negative pressure in the dialysis fluid circuit.

10 Claims, 3 Drawing Sheets

(58) Field of Classification Search
CPC .... A61M 1/16; A61M 1/1601; A61M 1/1615;
A61M 1/1613
See application file for complete search history.

(56) References Cited

U.S. PATENT DOCUMENTS

| 10,376,628 | B2 | 8/2019 | Blasek et al. |
| 10,493,196 | B2 | 12/2019 | Riemenschneider |
| 2002/0142083 | A1 | 10/2002 | Jacobs |
| 2010/0087772 | A1* | 4/2010 | Gronau ............... A61M 1/3646 |
| | | | 604/6.11 |
| 2010/0168640 | A1 | 7/2010 | Kopperschmidt et al. |
| 2010/0192686 | A1* | 8/2010 | Kamen ............... A61M 1/3672 |
| | | | 715/764 |
| 2016/0250406 | A1 | 9/2016 | Parisotto et al. |
| 2017/0258975 | A1* | 9/2017 | Fulkerson ............... A61M 1/14 |
| 2017/0296733 | A1* | 10/2017 | Riemenschneider ........................ |
| | | | A61M 1/3626 |
| 2019/0001043 | A1 | 1/2019 | Spickermann et al. |
| 2019/0160218 | A1 | 5/2019 | Spickermann et al. |
| 2019/0358389 | A1* | 11/2019 | Thys ................... A61M 1/3646 |
| 2020/0230301 | A1 | 7/2020 | Beisser et al. |
| 2020/0338255 | A1* | 10/2020 | Hobro ................. A61M 1/3646 |
| 2020/0353148 | A1* | 11/2020 | Chamney ............. A61M 1/282 |
| 2021/0178046 | A1* | 6/2021 | Hobro ................. A61M 1/1672 |

FOREIGN PATENT DOCUMENTS

| CN | 108697990 | A | 10/2018 |
| CN | 109475675 | A | 3/2019 |
| DE | 102011108785 | A1 | 1/2013 |
| DE | 102013011717 | A1 | 1/2015 |
| EP | 2583701 | A1 | 4/2013 |
| EP | 3231466 | B1 | 8/2019 |
| WO | 2007104447 | A1 | 9/2007 |

OTHER PUBLICATIONS

Search Report received in German Application No. 10 2020 126 303.1 dated Jun. 21, 2021, with translation, 12 pages.
Search Report received in International Application No. PCT/EP2021/077052 dated Dec. 3, 2021, with translation, 5 pages.
Written Opinion received in International Application No. PCT/EP2021/077052 dated Dec. 3, 2021, with translation, 12 pages.
Notification received in Chinese Application No. 202180068955.9 dated Dec. 17, 2025, with translation, 10 pages.

* cited by examiner

| S1 | S2 | S3 | S4 |
|---|---|---|---|
| 43 s | 154 s | 493 s | 573 s |
| 543.8 g | 381.1 g | 359.2 g | 357.9 g |

AUTOMATIC EMPTYING OF A DIALYZER FOLLOWING A BLOOD TREATMENT THERAPY

CROSS-REFERENCE TO RELATED APPLICATIONS

This application is the United States national phase entry of International Application No. PCT/EP2021/077052, filed Oct. 1, 2021, and claims priority to German Application No. 10 2020 126 303.1, filed Oct. 7, 2020. The contents of International Application No. PCT/EP2021/077052 and German Application No. 10 2020 126 303.1 are incorporated by reference herein in their entireties.

FIELD

The present disclosure relates to an extracorporeal blood treatment device, in particular a dialysis device, for use in a blood treatment therapy, comprising: an extracorporeal circuit; a dialysis liquid circuit; and a dialyzer comprising a blood side which is fluidically connected to the extracorporeal circuit, and a dialysis liquid side which is fluidically connected to the dialysis liquid circuit, wherein the blood side of the dialyzer and the dialysis liquid side of the dialyzer are separated from each other via a membrane provided in the dialyzer, and the extracorporeal blood treatment device further comprises a control unit which is adapted to automatically empty the dialyzer after an end of the blood treatment therapy by setting a negative pressure or, respectively, an underpressure in the dialysis liquid circuit and a concomitant transfer of a liquid from the blood side via the membrane of the dialyzer into the dialysis liquid side. Furthermore, the present disclosure relates to a method for automatically emptying a dialyzer after an end of blood treatment therapy.

BACKGROUND

After a completed blood treatment therapy, in which blood of a patient has been purified extracorporeally using a dialyzer and, if applicable, a dialysis liquid flowing through the dialyzer, the blood of the patient, which is still in an extracorporeal circuit, for example in an arterial and venous hose system (A/V hose system), is generally returned to the patient. This process is called reinfusion. Only when the blood still present in the extracorporeal circuit has been suitably returned/reinfused to the patient, is the patient completely uncoupled from the extracorporeal hose system (both arterial and venous). After the reinfusion, there is basically still (reinfusion) liquid in the extracorporeal circuit, the dialyzer, etc. Before the hoses forming the extracorporeal circuit and the dialysis liquid circuit and the dialyzer are disposed of, they should be emptied, in particular to reduce the (weight-dependent) disposal costs.

In the prior art, extracorporeal blood treatment devices are known which require several manual steps to be performed by a user when emptying a dialyzer after the end of a blood treatment therapy and after reinfusion of the patient's blood. For example, it is known that first the extracorporeal circuit or the blood hose system is uncoupled from the dialyzer and is emptied into a bag or into a waste port of the blood treatment device. Subsequently, a dialysis liquid inflow hose can be uncoupled from the dialyzer and any liquid still present in the dialyzer can be at least partially sucked out via the dialysis liquid outflow hose.

This semi-automatic emptying disadvantageously requires several steps to be performed manually. The nursing staff has to interact with the extracorporeal blood treatment device several times, which in particular also results in a waiting time in front of the machine. Furthermore, although the dialysis liquid side of the dialyzer is suitably freed from the liquid still present in it by this emptying method, the blood side of the dialyzer is not. As a result, the weight of the dialyzer is still very high after emptying, which is accompanied by high disposal costs.

EP 3 231 466 B1 describes automated emptying of an extracorporeal circuit/A/V hose system and a blood side of the dialyzer. An underpressure is generated on the dialysis liquid side of the dialyzer via which a liquid is extracted from the blood side of the dialyzer so that the liquid passes from the blood side to the dialysis liquid side via a membrane of the dialyzer. The liquid transfer is supported by a gauge or level regulation pump provided in the extracorporeal circuit. During the emptying process, the ends of the arterial portion of the extracorporeal circuit and of the venous portion of the extracorporeal circuit are short-circuited and at least one blood pump provided in the extracorporeal circuit is in operation, so that the liquid present in the short-circuited blood circuit is conveyed in the therapy flow direction into the blood side of the dialyzer, where it passes into the dialysis liquid side of the dialyzer due to the pressure drop and is withdrawn.

EP 3 231 466 B1 does not deal with emptying the dialysis liquid side of the dialyzer. Against this background, it can be assumed that even after the emptying of the blood side of the dialyzer and the extracorporeal circuit described in EP 3 231 466 B 1, several manual steps are required (uncoupling of the extracorporeal circuit from the dialyzer, uncoupling of the dialysis liquid inflow hose from the dialyzer; draining of the liquid still present in the dialyzer via the dialysis liquid outflow hose). Therefore, although a weight of the dialyzer can be reduced after emptying using the disclosure of EP 3 231 466 B1, several manual steps are still required by the user.

Finally, fully automatic emptying of a dialyzer after a blood treatment therapy is already known from EP 1 996 253 B1. According to the disclosure of EP 1 996 253 B1, the blood side of the dialyzer and the extracorporeal circuit are first emptied in a similar manner as in EP 3 231 466 B1. Subsequently, the dialysis liquid side of the dialyzer is also emptied automatically. For this purpose, a (vent) valve located in the dialysis liquid inflow is opened. When a fluid pump located in the dialysis liquid outflow is activated, air can flow into the dialyzer (possibly supported by a compressor located in the dialysis liquid inflow) so that the liquid still on the dialysis liquid side of the dialyzer is transported to the dialyzer exit until the entire dialyzer is filled with air.

In EP 1 996 253 B1, an additional vent valve is disadvantageously required to be able to provide fully automatic emptying of the dialyzer.

Both EP 1 996 253 B1 and EP 3 231 466 B1 disclose an extracorporeal blood treatment device.

SUMMARY

Against this background, the object of the present disclosure is to avoid or at least reduce the disadvantages of the prior art. In particular, a dialyzer is to be emptied completely automatically after the end of a blood treatment therapy in order to reduce a disposal weight of the dialyzer to a minimum. Furthermore, interaction of the nursing staff with the extracorporeal blood treatment device is to be reduced.

In addition, for automatic emptying, preferably only the components already present as standard in an extracorporeal blood treatment device are to be used/required.

The disclosure first relates to an extracorporeal blood treatment device for use in a blood treatment therapy, comprising: an extracorporeal circuit; a dialysis liquid circuit; and a dialyzer comprising a blood side fluidically connected to the extracorporeal circuit, and a dialysis liquid side fluidically connected to the dialysis liquid circuit, wherein the blood side of the dialyzer and the dialysis liquid side of the dialyzer are separated from each other via a membrane provided in the dialyzer, and the extracorporeal blood treatment device further comprises a control unit configured to automatically empty the dialyzer after an end of the blood treatment therapy by setting a negative pressure or underpressure in the dialysis liquid circuit, and a concomitant transfer of a liquid from the blood side via the membrane of the dialyzer into the dialysis liquid side. The control unit is configured, when the liquid from the extracorporeal circuit has completely transferred from the blood side via the membrane of the dialyzer into the dialysis liquid side and the blood side of the dialyzer is emptied, by a continued adjustment of the negative pressure or underpressure in the dialysis liquid circuit, to cause a transfer of air from the blood side via the membrane of the dialyzer to the dialysis liquid side and a displacement of the liquid out of the dialysis liquid side of the dialyzer to a dialysis liquid outflow (downstream of the dialyzer), in order to also automatically empty the dialysis liquid side of the dialyzer.

According to the present disclosure, after an end of the blood treatment therapy, the control unit preferably first controls a reinfusion of blood into the patient such that a (dialysis) liquid is delivered from the dialysis liquid circuit via the membrane of the dialyzer to the extracorporeal circuit, which upon reinfusion displaces the blood present in the extracorporeal circuit towards a patient in order to return the blood to the patient via both the venous portion and the arterial portion.

Preferably, the control unit is configured to close an arterial hose clamp provided in the arterial portion of the extracorporeal circuit and a venous hose clamp provided in the venous portion of the extracorporeal circuit when reinfusion (via both the arterial portion of the extracorporeal circuit and the venous portion of the extracorporeal circuit) has been stopped.

Advantageously, nursing staff subsequently uncouples the patient both from the arterial and venous sides.

After uncoupling the patient, one end/patient-side connection of the arterial portion is preferably short-circuited or connected to one end/patient-side connection of the venous portion. Advantageously, this represents the last active interaction of the nursing staff with the extracorporeal blood treatment device. In other words, according to the disclosure, it is provided that complete automatic emptying of the dialyzer controlled by the control unit is subsequently performed without the nursing staff having to interact with the extracorporeal blood treatment device again.

It is furthermore practical when the dialyzer is arranged or oriented during automatic emptying thereof on the extracorporeal blood treatment device such that a dialysis liquid exit connected to the dialysis liquid outflow is arranged (in a height direction/vertical direction/upward direction of the extracorporeal blood treatment device) below a dialysis liquid inlet connected to a dialysis liquid inflow.

In other words, during automatic emptying of the dialyzer, the dialyzer is preferably arranged/oriented on the extracorporeal blood treatment device in such a way that a dialysis liquid exit is located at the bottom and a dialysis liquid inlet is located at the top. Particularly preferably, the dialyzer is oriented vertically, that is, a longitudinal axis of the substantially cylindrical dialyzer preferably extends in a vertical direction (perpendicular to the surface of the earth).

When it is basically provided in an extracorporeal blood treatment device that the dialyzer exit is at the top and not at the bottom during blood treatment therapy (for example, due to the countercurrent principle), it is necessary for the nursing staff to rotate the dialyzer before automatic emptying, i.e., orienting it so that the dialysis liquid exit is at the bottom. This manual step, to be performed if necessary, can be performed by the nursing staff together with the short-circuiting of the extracorporeal circuit, so that preferably no additional interaction associated with a waiting time of the nursing staff is required.

In an advantageous manner, following the uncoupling of the patient and the possible turning of the dialyzer, automatic emptying of the blood side of the dialyzer is first carried out. In particular, the method described in EP 3 231 466 B1 may be carried out, which provides a suitable method for emptying the blood hose system and the blood-side dialyzer/the blood side of the dialyzer. In particular, the control unit is thus configured to create/generate a negative pressure or underpressure in the dialysis liquid circuit (on the dialysis liquid side), whereby a (dialysis) liquid present in the extracorporeal circuit (on the blood side) is drained. During emptying, the liquid (still present in the extracorporeal circuit) is preferably delivered from the extracorporeal circuit via the membrane of the dialyzer to the dialysis liquid circuit until no more liquid is present in the extracorporeal circuit and the blood side of the dialyzer.

The core of the disclosure is that the control unit is configured to control the emptying of the dialyzer in such a way that first the liquid and then (when the liquid from the extracorporeal circuit has completely passed via the membrane of the dialyzer from the blood side to the dialysis liquid side, i.e., there is no more liquid in the extracorporeal circuit and the blood side of the dialyzer), air passes from the extracorporeal circuit/the blood side via the membrane of the dialyzer to the dialysis liquid circuit/dialysis liquid side, so that the dialysis liquid is also displaced by the transferring air from the dialysis liquid side of the dialyzer to the dialysis liquid outflow.

In particular, it has been found in accordance with the present disclosure that when the liquid from the extracorporeal circuit has completely passed from the blood side via the membrane of the dialyzer into the dialysis liquid side and the blood side of the dialyzer has been emptied, it can be achieved by continuing to adjust the negative pressure or underpressure in the dialysis liquid circuit (suction pressure on the dialysis liquid side) that air slowly passes from the blood side via the membrane of the dialyzer to the dialysis liquid side. If the dialyzer is oriented in such a way that the dialyzer exit or the dialysis liquid outflow is at the bottom and the dialyzer inlet or dialysis liquid inflow is at the top, the transferred air collects in an upper portion of the dialyzer (near the dialyzer inlet), displaces the liquid downward toward the dialyzer exit and pushes the liquid still present in the dialysis liquid side out of the dialyzer via the dialyzer exit.

The control unit is thus configured for complete automatic emptying of the dialyzer after an end of the blood treatment therapy.

Preferably, the control unit is configured to generate the negative pressure or underpressure in the dialysis liquid circuit such that a flux-pump outlet, which is a fluid pump in the dialysis liquid outflow of the dialysis liquid circuit (downstream of the dialyzer), is driven to pump the liquid or air (from the blood side via the membrane of the dialyzer into the dialysis liquid side and finally) out of/away from the dialyzer into the dialysis liquid outflow.

Advantageously, the control unit is configured to drive/actuate a compressor pump provided in the extracorporeal circuit to support the transfer of the liquid and/or air from the blood side via the membrane of the dialyzer to the dialysis liquid side. In particular, the control unit is configured to drive the compressor pump in such a way that it pushes the liquid and the air through the membrane of the dialyzer.

Advantageously, the control unit is furthermore configured to control or regulate a transmembrane pressure of the dialyzer during automatic emptying of the dialyzer to a pressure that is greater than a predetermined value and smaller than a dialyzer-specific, maximum permissible transmembrane pressure. The maximum permissible transmembrane pressure depends in particular on the type of dialyzer/the dialyzer used and is generally specified in the data sheets of dialyzers.

Preferably, the control unit is configured to control or regulate the transmembrane pressure of the dialyzer to a pressure greater than 400 mmHg, preferably greater than 500 mmHg. For example, the transmembrane pressure is controlled/regulated by the control unit to a pressure between 500 mmHg and 600 mmHg, for example 550 mmHg, but only if the maximum permissible transmembrane pressure is not yet exceeded at the set pressure. It is absolutely necessary to ensure that the maximum permissible transmembrane pressure is not exceeded. Preferably, the extracorporeal blood treatment device of the present disclosure may also use only dialyzers whose maximum permissible transmembrane pressure is at least greater than 600 mmHg.

According to the present disclosure, it has been found in particular that if an underpressure is generated on the dialysis liquid side (by driving the flux-pump outlet) possibly together with an overpressure on the blood side (by driving the compressor pump) in such a way that a constant and high transmembrane pressure is present, which is in the range described above, air passes (relatively slowly) through the membrane of the dialyzer when the extracorporeal circuit is already empty and also displaces the dialysis liquid still present on the dialysis liquid side of the dialyzer from the dialyzer.

Preferably, the control unit is configured to stop the automatic emptying of the dialysis liquid side of the dialyzer in a sensor-controlled/sensor-regulated manner.

According to a preferred configuration example, the control unit is configured to evaluate a pressure signal or a pressure course of a pressure sensor arranged in the dialysis liquid outflow, which measures or monitors a pressure in the dialysis liquid outflow, and to stop the automatic emptying of the dialysis liquid side based on the pressure signal or the pressure course of the pressure sensor.

The control unit is preferably configured to evaluate a slope or a first derivative of the pressure signal or of the pressure course of the pressure sensor, and to stop the automatic emptying of the dialysis liquid side if the slope or first derivative of the pressure signal or of the pressure course falls below a predetermined first limit value. In particular, according to the disclosure, it has been found that air is present in the dialysis liquid outflow when the slope/first derivative of the pressure signal or of the pressure course of the pressure sensor becomes negative.

According to an alternative, preferred configuration example, the control unit may also be configured to stop the automatic emptying of the dialysis liquid side in a sensor-controlled manner if an air separator provided or arranged in the dialysis liquid circuit detects or measures that a liquid level of the air separator has fallen below a predetermined liquid level or gauge height.

Alternatively or additionally, the control unit may also be configured to stop the automatic emptying of the dialysis liquid side of the dialyzer in a time-controlled/time-regulated manner. In particular, a control system that combines a sensor-controlled stop with a time-controlled stop is also conceivable.

Furthermore, the present disclosure relates to a method for automatically emptying a dialyzer after an end of a blood treatment therapy, in particular performed or to be performed in an extracorporeal blood treatment device as described above, comprising the steps of: setting a negative pressure or underpressure in a dialysis liquid circuit and concomitant transfer of a liquid from a blood side of the dialyzer via a membrane of the dialyzer into a dialysis liquid side of the dialyzer; and, when the liquid from an extracorporeal circuit has completely passed from the blood side via the membrane of the dialyzer into the dialysis liquid side and the blood side of the dialyzer is emptied, continuing to adjust the negative pressure or underpressure in the dialysis liquid circuit to cause transfer of air from the blood side via the membrane of the dialyzer to the dialysis liquid side and displacement of the liquid out of the dialysis liquid side of the dialyzer to a dialysis liquid outflow in order to also automatically empty the dialysis liquid side of the dialyzer.

Preferably, the method further comprises the step of: arranging or orienting the dialyzer during automatic emptying thereof on the extracorporeal blood treatment device such that a dialysis liquid exit connected to the dialysis liquid outflow is arranged (in a height direction/vertical direction/upward direction of the extracorporeal blood treatment device) below a dialysis liquid inlet connected to a dialysis liquid inflow.

Advantageously, the method further comprises the step of: generating the negative pressure or underpressure in the dialysis liquid circuit by pumping the liquid or air out of the dialyzer into the dialysis liquid outflow via a flux-pump outlet, which is a fluid pump in the dialysis liquid outflow of the dialysis liquid circuit.

Preferably, the method further comprises the step of: supporting the transfer of liquid or air from the blood side via the membrane of the dialyzer to the dialysis liquid side by a compressor pump provided in the extracorporeal circuit.

In particular, the method further comprises the following step: controlling or regulating a transmembrane pressure of the dialyzer to a pressure which is greater than a predetermined value and less than a dialyzer-specific maximum allowable transmembrane pressure. Preferably, the method additionally comprises the step of: controlling or regulating the transmembrane pressure of the dialyzer to a pressure which is greater than 400 mmHg, preferably greater than 500 mmHg.

It is advantageous if the method furthermore includes the following step: sensor-controlled stop of automatic emptying of the dialysis liquid side of the dialyzer.

Preferably, the method furthermore comprises the following steps: evaluating a pressure signal or a pressure course of a pressure sensor arranged in the dialysis liquid outflow, which measures or monitors a pressure in the dialysis liquid outflow, and stopping the automatic emptying of the dialysis liquid side based on the pressure signal or the pressure course of the pressure sensor.

Further preferably, the method comprises the steps of: evaluating a slope or a first derivative of the pressure signal or of the pressure course of the pressure sensor, and stopping the automatic emptying of the dialysis liquid side if the slope or first derivative of the pressure signal or the pressure course falls below a predetermined first limit value.

Alternatively, the method preferably comprises the step of: sensor-controlled stopping of the automatic emptying of the dialysis liquid side when it is detected or measured by an air separator provided or arranged in the dialysis liquid circuit that a liquid level of the air separator has fallen below a predetermined liquid level or gauge height.

Alternatively or additionally, the method preferably comprises the following step: time-controlled stop of the automatic emptying of the dialysis liquid side of the dialyzer.

When the method according to the disclosure is performed, preferably one end of the arterial portion of the extracorporeal circuit is connected to one end of the venous portion of the extracorporeal circuit so that a patient is already uncoupled. The method according to the disclosure thus does not relate to a method for surgical or therapeutic treatment of the human body.

BRIEF DESCRIPTION OF THE DRAWINGS

The present disclosure is further explained below with reference to figures. The following is shown.

DETAILED DESCRIPTION

The figures are merely schematic in nature and are intended solely for the purpose of understanding the disclosure. Identical elements are provided with the same reference signs. The features of the individual configuration examples can be interchanged unless explicitly described otherwise.

Figures 1, 2:
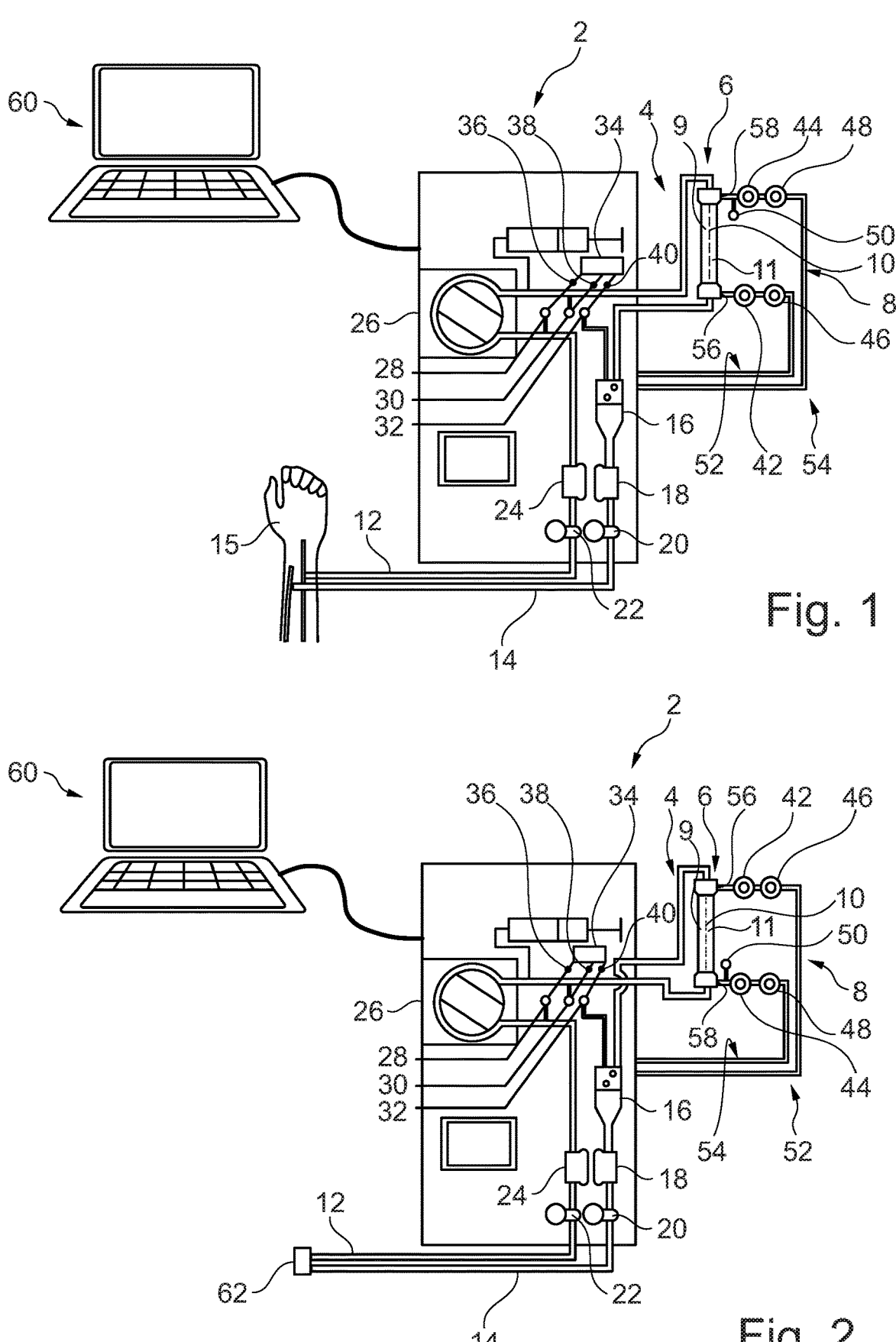
FIG. 1 shows an extracorporeal blood treatment device according to the present disclosure during a blood treatment therapy or during a reinfusion, respectively.
FIG. 2 shows the extracorporeal blood treatment device according to the present disclosure during automatic emptying of a dialyzer.

FIG. 1 shows an extracorporeal blood treatment device (dialysis device) 2 during a blood treatment therapy or respectively during reinfusion, i.e. before automatic emptying according to the disclosure.

The extracorporeal blood treatment device 2 basically comprises an extracorporeal circuit (A/V hose system) 4, a dialyzer 6, and a dialysis liquid circuit 8. A blood side 9 of the dialyzer 6 is separated from a dialysis liquid side 11 of the dialyzer 6 by a (hollow fiber) membrane 10.

The extracorporeal circuit 4 includes an arterial portion 12 located upstream of the dialyzer 6, and a venous portion 14 located downstream of the dialyzer 6.

As shown in FIG. 1, the arterial portion 12 and the venous portion 14 are coupled to a patient 15. In other words, one end of the arterial portion 12 is coupled to an artery of the patient 15 and one end of the venous portion 14 is coupled to a vein of the patient 15.

In the venous portion 14 of the extracorporeal circuit 4, downstream of the dialyzer 6 (that is, starting from the dialyzer 6 in a direction toward the end of the venous portion 14), a venous expansion chamber or air trap 16, a venous safety air detector 18, and a venous hose clamp 20 are provided.

In the arterial portion 12, starting from the patient-side end of the arterial portion 12 in a direction towards the dialyzer 6, an arterial hose clamp 22, an arterial safety air detector 24 and an (arterial) blood pump 26 are provided. As can be seen in FIG. 1, the extracorporeal circuit 4 (in particular a blood pump adapter thereof) is already inserted into the blood pump 26, which is preferably in the form of a roller pump or peristaltic pump and is configured to deliver a fluid/liquid by squeezing a hose.

In the arterial portion 12, an arterial pressure upstream or respectively before the blood pump 26 can be measured by an arterial pressure sensor 28. Furthermore, a dialyzer-inlet pressure can be measured downstream or after the blood pump 26 and upstream or before the dialyzer 6 (between dialyzer 6 and blood pump 26) via a dialyzer-inlet pressure sensor 30. In the venous portion 14, venous pressure at/downstream of the venous expansion chamber or air trap 16 can be measured via a venous pressure sensor 32. The pressure sensors 28, 30, 32 provided in the extracorporeal circuit 4 can measure/pick up/monitor the pressure at the respective locations in the extracorporeal circuit 4 where they are arranged/provided.

As can be seen furthermore from FIG. 1, a compressor pump or a gauge or level regulation pump (LRP) 34 is located behind the arterial pressure sensor 28, the dialyzer-inlet pressure sensor 30, and the venous pressure sensor 32 and has associated valves 36, 38, 40, that is a first valve 36 between the arterial pressure sensor 28 and the compressor pump 34, a second valve 38 between the dialyzer-inlet pressure sensor 30 and the compressor pump 34, and a third valve 40 between the venous pressure sensor 32 and the compressor pump 34.

The dialysis liquid circuit 8 includes a dialyzer inlet valve 42, a dialyzer outlet valve 44, a flux-pump inlet 46, a flux-pump outlet 48, and a pressure sensor 50. The dialyzer inlet valve 42 and the flux-pump inlet 46 are provided/arranged at a dialysis liquid inflow 52 upstream of the dialyzer 6. The pressure sensor 50, the dialyzer outlet valve 44 and the flux-pump outlet 48 are provided/arranged at a dialysis liquid outflow 54 downstream of the dialyzer 6. The flux-pump inlet 46 and the flux-pump outlet 48 are preferably gear pumps. The dialysis liquid inflow 52 is coupled to a dialyzer inlet 56 of the dialyzer 6. The dialysis liquid outflow 54 is coupled to a dialyzer exit 58 of the dialyzer 6.

The extracorporeal blood treatment device 2 furthermore comprises a control unit 60, which is preferably in the form of a processor, in particular a central processing unit (CPU). The control unit 60 is preferably integrated into the extracorporeal blood treatment device 2, i.e. it is not separated from the extracorporeal blood treatment device 2. The control unit 60 receives information from sensors which are provided in the extracorporeal blood treatment device 2. The sensors shown in FIG. 1 are merely examples, i.e., the arterial pressure sensor 28, the dialyzer-inlet pressure sensor 30, the venous pressure sensor 32, the arterial safety air detector 24, the venous safety air detector 18, and the pressure sensor 50, etc. On the other hand, the control unit 60 controls or actuates actuators which are provided in the extracorporeal blood treatment device 2. The valves, pumps, hose clamps, etc. shown in FIG. 1, i.e. in particular the dialyzer inlet valve 42, the dialyzer outlet valve 44, the flux-pump inlet 46, the flux-pump outlet 48, the (arterial) blood pump 26, the arterial hose clamp 22, the venous hose clamp 20, etc. are merely examples.

After the end of the blood treatment therapy, the control unit 60 first controls a reinfusion of blood into the patient 15 in such a way that a (dialysis) liquid is supplied from the dialysis liquid circuit 8 via the membrane 10 of the dialyzer 6 to the extracorporeal circuit 4, which during the reinfusion displaces the blood still present in the extracorporeal circuit 4 towards the patient 15 in order to return the blood to the patient 15 both via the venous portion 14 and via the arterial portion 12. Advantageously, a positive pressure is built up on the dialysis liquid side 11 in order to force the liquid through the membrane 10 of the dialyzer 6 into the blood side 9. In addition, underpressure can be built up on the blood side 9 in order to draw the liquid into the blood side 9 via the membrane of the dialyzer 6.

In order to stop the reinfusion via both the arterial portion 12 of the extracorporeal circuit 4 and the venous portion 14 of the extracorporeal circuit 4 (when the blood has been completely reinfused), the control unit 46 closes the arterial hose clamp 22 as well as the venous hose clamp 20. Subsequently, the patient 15 is uncoupled both arterially and venously by the nursing staff.

FIG. 2 shows the extracorporeal blood treatment device (dialysis device) 2 during automatic emptying of the dialyzer 6. It can be seen that after uncoupling the patient 15, the arterial portion 12 and the venous portion 14 are short-circuited or fluidically connected to each other, for example via a connector/adapter 62. The dialyzer 6 has been turned by the nursing staff to enable automatic emptying, so that in FIG. 2 the dialyzer exit 58 is at the bottom and the dialyzer inlet 56 is at the top. The dialyzer 6 is advantageously oriented vertically during automatic emptying.

The control of automatic emptying of the dialyzer 6 performed by the control unit 60 is described with reference to FIG. 2.

Preferably, the control unit 60 is configured to first create or establish an underpressure on the dialysis liquid side 11 of the dialyzer 6. For this purpose, the control unit 60 controls the flux-pump outlet 48 to pump the liquid present in the extracorporeal circuit 4 and in the blood side 9 of the dialyzer 6 into the dialysis liquid side 11 of the dialyzer 6 and out of the dialyzer 6 into the dialysis liquid outflow 54. In this process, the flux-pump inlet 46 is preferably stopped, the dialyzer inlet valve 42 is closed, and the dialyzer outlet valve 44 is opened.

Furthermore, the control unit 60 may drive the compressor pump 34 to support the transfer of liquid from the blood side 9 via the membrane 10 of the dialyzer 6 to the dialysis liquid side 11. In order to do this, the compressor pump 34 preferably pushes air into the extracorporeal circuit 4. For example, the third valve 40 is opened while the first valve 36 and the second valve 38 remain closed, and the compressor pump 34 pumps air into the venous expansion chamber/air trap 16 (control/regulation of the air supply via the venous pressure sensor 32). This injection of air into the extracorporeal circuit 4 builds up a pressure in the extracorporeal circuit 4 and the liquid still present in the extracorporeal circuit 4 is additionally also pressed via the membrane 10 of the dialyzer 6 from the blood side 9 into the dialysis liquid side 11.

According to the present disclosure, actuation of the compressor pump 34 during automatic emptying of the dialyzer 6 is optional, i.e. not mandatory.

In any case, however, the control unit 60 is configured to control or regulate a transmembrane pressure of the dialyzer 6 to a constant, high value. In particular, it has been found that the transmembrane pressure should be greater than 400 mmHg, in particular greater than 500 mmHg, for example 550 mmHg. The transmembrane pressure may be controlled/regulated by the control unit 60 merely by controlling the flux-pump outlet 48 (for example, changing the delivery rate thereof). In other words, basically only a suitable negative pressure can be generated on the dialysis liquid side 11. Alternatively, an overpressure can also be generated on the blood side 9 by additionally controlling the compressor pump 34.

The transmembrane pressure is controlled or regulated by the control unit 60 in any case so as not to exceed the maximum permissible transmembrane pressure of the dialyzer 6 used, which is entered or read in by a user before a blood treatment therapy, for example, and is thus known to the blood treatment device 2, in particular to the control unit 60. In particular, this prevents hollow fibers of the membrane 10 from tearing, and thus prevents any blood particles still present in the liquid from passing into the dialysis liquid side 11.

According to the present disclosure, when the liquid from the extracorporeal circuit 4 has completely passed from the blood side 9 via the membrane 10 of the dialyzer 6 into the dialysis liquid side 11, and the blood side 9 of the dialyzer 6 has been emptied, the underpressure already present on the dialysis liquid side 11, or in particular the controlled/regulated transmembrane pressure, is maintained. In particular, according to the disclosure, it has been found that when the transmembrane pressure is controlled/regulated to such a high value, both liquid and air can be transported via the membrane 10 of the dialyzer 6. At this point at the latest, the dialyzer exit 58 has to be at the bottom/directed downwards. Due to the prevailing underpressure and an emptied extracorporeal circuit 4, air now passes through the membrane 10 of the dialyzer 6 and also displaces the liquid still present in the dialyzer 6 out of the dialysis liquid side 11 toward the dialysis liquid outflow 54. The air transfer is also preferably supported by the compressor pump 34.

Figures 3, 4:
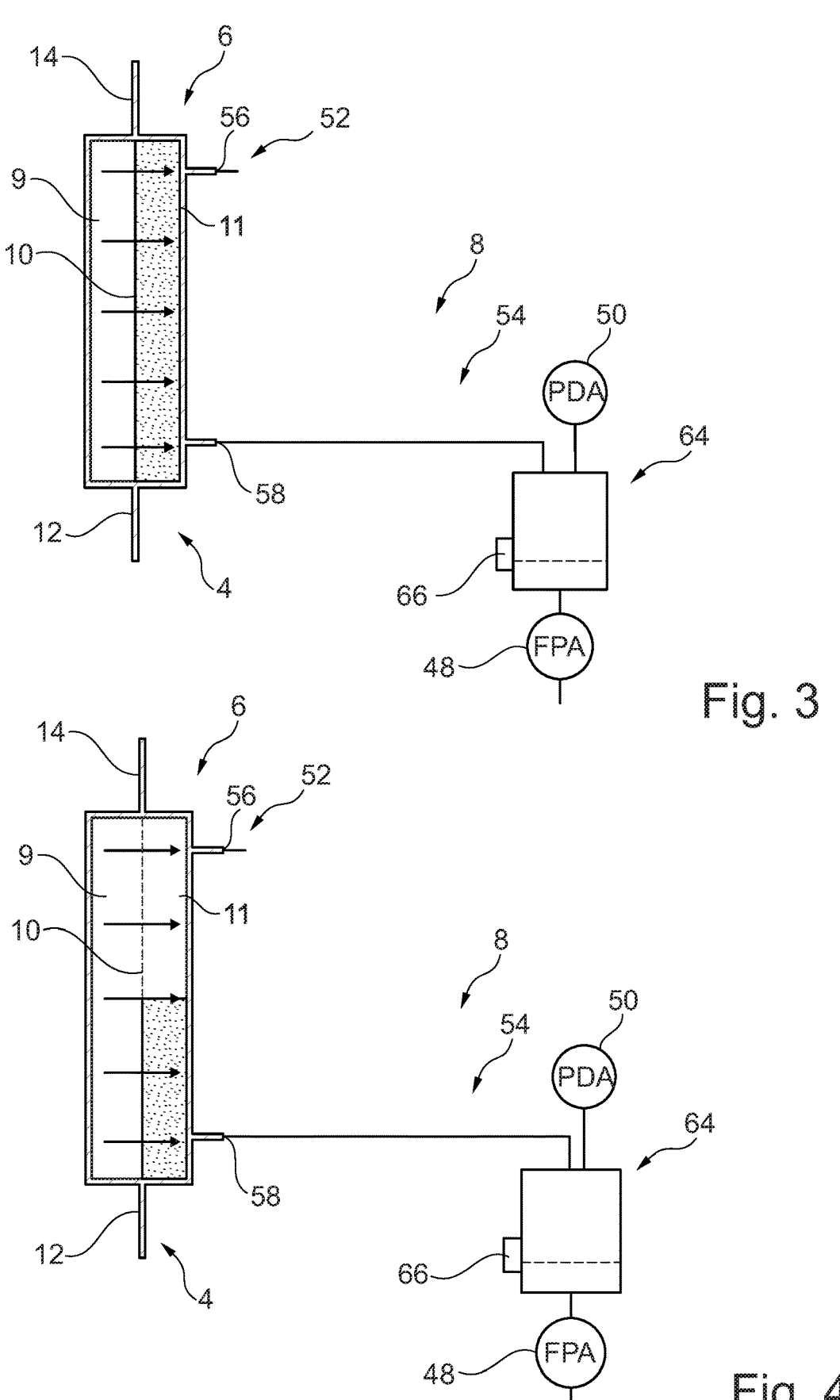
FIG. 3 shows a detailed view of the dialyzer in a state in which a blood side of the dialyzer is already completely emptied.
FIG. 4 shows a detailed view of the dialyzer in a state in which a dialysis liquid side of the dialyzer is being emptied.

FIG. 3 shows a detailed view of the dialyzer 6 in a state in which the blood side 9 thereof is already completely emptied. FIG. 4 shows a detailed view of the dialyzer 6 in a state in which the dialysis liquid side 11 thereof is being emptied. As can be seen in particular from FIG. 4, the excess air initially collects in an upper portion of the dialyzer 6 (in the area of/near the dialyzer inlet 56) and displaces the liquid downward toward the dialyzer exit 58.

The control unit 60 is preferably configured to stop automatic emptying of the dialyzer 6 when the dialysis liquid side 11 of the dialyzer 6 is also completely emptied. Preferred stop criteria of the present disclosure are at first described with reference to FIG. 3 and FIG. 4.

In principle, a time-controlled stop of the automatic emptying is conceivable according to the present disclosure. For example, the control unit 60 may detect when the blood side 9 of the dialyzer 6 is completely emptied based on sensor data transmitted to it. If the control unit 60 knows how long emptying of the dialysis liquid side 11 usually takes for the dialyzer 6 used at the set transmembrane pressure, the control unit 60 can stop the automatic emptying when a corresponding time period has elapsed.

According to the present disclosure, a sensor-controlled stop of the automatic emptying of the dialysis liquid side 11 of the dialyzer 6 is particularly preferred. In this context, the control unit 60 advantageously evaluates a pressure signal or a pressure course of the pressure sensor 50 arranged in the dialysis liquid outflow 54.

Alternatively, the sensor-controlled stop of the automatic emptying may also take place via an air separator 64 provided in the dialysis liquid circuit 8, in particular in the dialysis liquid outflow 54. The air separator 64 basically serves to remove air from dialysate during blood treatment therapy and protects the flux pump outlet 48 from unwanted air entry. At least one liquid-level sensor 66 is provided in the air separator 64. When the liquid-level sensor 66 of the air separator 64 detects that the liquid level in the air separator 64 has fallen below a predetermined liquid level or gauge height, this means that air has entered the air separator 64 via the dialysis liquid outflow 54 and thus the dialysis liquid side 11 of the dialyzer 6 has also been emptied.

Since there is a relatively long hose portion between the dialyzer 6 and the air separator 64 in practice (about 1 meter), it takes a very long time for the automatic emptying to stop when the air separator 64 is used for the sensor-controlled stop. In view of this, the use of the pressure sensor (PDA) 50 is generally preferred with respect to the sensor-controlled stop according to the present disclosure. This is because a period of time after which the pressure change has been transmitted through the hose portion is substantially shorter than a period of time after which air has entered the air separator 64 via the dialysis liquid outflow 54. Even though both FIG. 3 and FIG. 4 are essentially schematic views, it should nevertheless be made clear in both figures that the pressure sensor 50 and the air separator 64 are arranged at a distance from the dialyzer 6. According to the disclosure, it may also be provided that the air separator 64 and the pressure sensor 50 are combined in one component, as indicated in FIG. 3 and FIG. 4.

Figures 5, 6, 7:
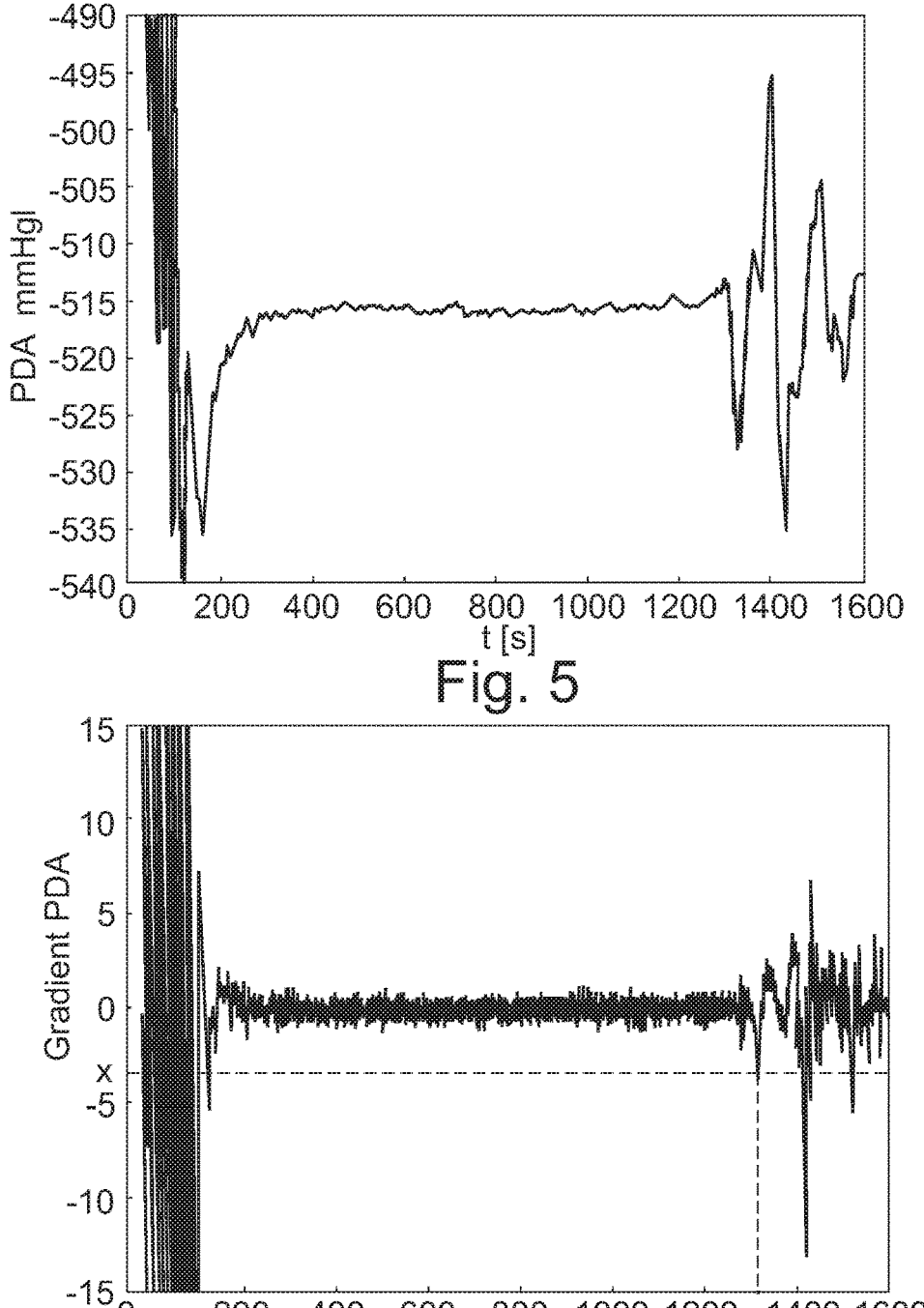
FIG. 5 shows a diagram in which a pressure signal or a pressure course of a pressure sensor arranged in the dialysis liquid outflow is shown over time.
FIG. 6 shows a diagram in which a first derivative of the pressure signal or pressure course of the pressure sensor is shown over time.
FIG. 7 shows a table in which a required time and a remaining disposal weight are indicated for different dialyzer emptying methods.

The sensor-controlled stop of the automatic emptying of the dialysis liquid side 11 of the dialyzer 6 is described in more detail with reference to FIG. 5 and FIG. 6. FIG. 5 shows a diagram in which the pressure signal or the pressure course of the pressure sensor 50 is shown over time. FIG. 6 shows a diagram in which a slope/first derivative/gradient of the pressure signal or of the pressure course of pressure sensor 50 over time is shown.

The control unit 60 preferably monitors the pressure measured by the pressure sensor (PDA) 50 toward the end of the emptying process, for example from about 200 seconds in FIG. 5 or FIG. 6. When the dialyzer 6 is completely emptied, air enters the dialysis liquid outflow 54. This is accompanied by a drop in pressure in the dialysis liquid outflow 54, wherein the drop is measured by the pressure sensor (PDA) 50. FIG. 5 and FIG. 6 show that the pressure measured by the pressure sensor 50 is almost constant during emptying. The same applies accordingly to the slope of the pressure signal. After approx. 1200 seconds, the signal in FIG. 5 starts to fluctuate. This is an indication that air is now (also) present at the pressure sensor 50. The slope of the pressure signal also changes (see FIG. 6). According to the present disclosure, it has been found that the stop of the automatic emptying of the dialyzer 6 is best performed based on the slope or first derivative of the pressure signal. When the slope falls below a certain negative predetermined value x, which is preferably set between -3 and -5, preferably to (about) -4, the stop criterion is fulfilled. This is the case in FIG. 6 at time t1.

Finally, FIG. 7 shows a table in which a required time and a remaining disposal weight are given for different dialyzer-emptying methods. The same dialyzer (available under registered trademark XEVONTA® HI23) was used for all experiments.

In the experiment designated 'S1', the extracorporeal circuit or the blood hose system was first uncoupled from the dialyzer and emptied into a bag or a waste port of the blood treatment device. Subsequently, a dialysis liquid inflow was uncoupled from the dialyzer and any liquid still present in the dialyzer was at least partially drained via the dialysis liquid outflow. This emptying method was shown to take only 43 seconds. The disposal weight was 543.8 grams.

In the experiment designated 'S2', dialyzer-emptying was performed as in the prior art of EP 1 996 253 B1, i.e., via a valve provided in the dialysis liquid inflow. This emptying method was shown to take 154 seconds. The disposal weight was 381.1 grams.

In the experiment designated 'S3', dialyzer emptying was performed according to the present disclosure, wherein a sensor-controlled stop of automatic emptying of the dialyzer was performed via the pressure sensor in the dialysis liquid outflow. This emptying method was shown to take 493 seconds. The disposal weight was reduced to 359.2 grams.

In the experiment designated 'S4', dialyzer emptying was performed in accordance with the present disclosure, wherein a sensor-controlled stop of the automatic emptying of the dialyzer was performed via the air separator in the dialysis liquid outflow. This emptying method was shown to take 573 seconds. The disposal weight was reduced to 357.9 grams.

It has thus been shown that, in accordance with the present disclosure (cf. experiments 'S3' and 'S4'), a reduction in disposal weight is possible compared with the prior art (applies in particular with regard to test 'S1', but also with regard to test 'S2'). Although the emptying of the dialyzer according to the present disclosure takes a long time, this disadvantage is readily accepted against the background of the achievable savings in disposal costs. Furthermore, it is true that the longer time period is not a significant factor in practice. This is because dialyzer emptying takes place automatically (i.e., without intervention by the nursing staff), and ultimately only the time after a patient has been uncoupled is used, in particular until the patient has left his or her treatment station.

The invention claimed is:

1. An extracorporeal blood treatment device for use in a blood treatment therapy, the extracorporeal blood treatment device comprising:
    an extracorporeal circuit;
    a dialysis liquid circuit including an air separator;
    a dialyzer comprising a blood side fluidically connected to the extracorporeal circuit and a dialysis liquid side fluidically connected to the dialysis liquid circuit; and
    a control unit,
    the blood side and the dialysis liquid side being separated from each other via a membrane provided in the dialyzer,
    the control unit being configured to automatically empty the dialyzer after an end of the blood treatment therapy by setting a negative pressure in the dialysis liquid circuit and a concomitant transfer of a liquid from the blood side via the membrane into the dialysis liquid side, the control unit being configured, when the liquid has completely transferred from the blood side via the membrane into the dialysis liquid side and the blood side of the dialyzer has been emptied, to cause, by a continued setting of the negative pressure in the dialysis liquid circuit, a transfer of air from the blood side via the membrane to the dialysis liquid side and a displacement of the liquid out of the dialysis liquid side of the dialyzer to a dialysis liquid outflow, in order to also automatically empty the dialysis liquid side of the dialyzer, and the control unit being configured to stop automatic emptying of the dialysis liquid side in a sensor-controlled manner when the air separator detects or measures that a liquid level of the air separator has fallen below a predetermined liquid level or gauge height.

2. The extracorporeal blood treatment device according to claim 1, wherein the dialyzer is arranged or oriented on the extracorporeal blood treatment device during automatic emptying of the dialyzer such that a dialysis liquid exit connected to the dialysis liquid outflow is arranged below a dialysis liquid inlet connected to a dialysis liquid inflow.

3. The extracorporeal blood treatment device according to claim 1, wherein the control unit is configured to generate the negative pressure in the dialysis liquid circuit such that a flux-pump outlet, which is a fluid pump in the dialysis liquid outflow of the dialysis liquid circuit, is driven to pump the liquid or air out of the dialyzer into the dialysis liquid outflow.

4. The extracorporeal blood treatment device according to claim 1, wherein the control unit is configured to drive or actuate a compressor pump provided in the extracorporeal circuit to support the transfer of the liquid or air from the blood side via the membrane to the dialysis liquid side.

5. The extracorporeal blood treatment device according to claim 1, wherein the control unit is configured to control or regulate a transmembrane pressure of the dialyzer during automatic emptying of the dialyzer to a pressure that is greater than a predetermined value and smaller than a dialyzer-specific, maximum permissible transmembrane pressure.

6. The extracorporeal blood treatment device according to claim 5, wherein the control unit is configured to control or regulate the transmembrane pressure of the dialyzer to a pressure greater than 400 mmHg.

7. The extracorporeal blood treatment device according to claim 1, wherein the control unit is configured to stop automatic emptying of the dialysis liquid side of the dialyzer in a time-controlled manner.

8. The extracorporeal blood treatment device according to claim 1, wherein the control unit is configured to:

evaluate a pressure signal or pressure course of a pressure sensor arranged in the dialysis liquid outflow, the pressure sensor configured to measure or monitor a pressure in the dialysis liquid outflow, and stop the automatic emptying of the dialysis liquid side based on the pressure signal or pressure course of the pressure sensor.

9. The extracorporeal blood treatment device according to claim 8, wherein the control unit is configured to:

evaluate a slope or a first derivative of the pressure signal or pressure course of the pressure sensor, and stop automatic emptying of the dialysis liquid side when the slope or the first derivative of the pressure signal or pressure course falls below a predetermined first limit value.

10. A method for automatically emptying a dialyzer after an end of a blood treatment therapy comprising the steps of:

setting a negative pressure in a dialysis liquid circuit and concomitant transfer of a liquid from a blood side of the dialyzer via a membrane of the dialyzer into a dialysis liquid side of the dialyzer;

continuing to set the negative pressure in the dialysis liquid circuit when the liquid from an extracorporeal circuit has completely passed from the blood side via the membrane of the dialyzer into the dialysis liquid side and the blood side of the dialyzer has been emptied, so as to cause a transfer of air from the blood side via the membrane of the dialyzer to the dialysis liquid side and a displacement of liquid out of the dialysis liquid side of the dialyzer to a dialysis liquid outflow in order to also automatically empty the dialysis liquid side of the dialyzer; and stopping the automatic emptying of the dialysis liquid side of the dialyzer in a sensor-controlled manner when a slope or a first derivative of a measured pressure signal or pressure course of a pressure sensor in the dialysis liquid outflow falls below a predetermined first limit value.

* * * * *